United States Patent [19]

Bernhart et al.

[11] 4,329,343
[45] May 11, 1982

[54] PYRROLE AMIDES AND THERAPEUTIC USE THEREOF

[75] Inventors: Claude Bernhart, St. Gely du Fesc; Jean P. Gagnol, St. Martin de Londres; Patrick Gautier, Cournonterral, all of France

[73] Assignee: Sanofi, Paris, France

[21] Appl. No.: 228,053

[22] Filed: Jan. 26, 1981

[51] Int. Cl.$^3$ .................... A61K 31/535; A61K 31/40; C07D 413/06; C07D 207/327
[52] U.S. Cl. ............................ 424/248.54; 424/250; 424/263; 424/267; 424/274; 544/131; 544/141; 544/349; 544/360; 544/372; 546/193; 546/208; 546/281; 548/561; 548/524
[58] Field of Search ............... 544/131, 141, 360, 372, 544/349; 546/193, 208, 281; 260/326.25, 326.43; 424/248.54, 250, 263, 267, 274

[56] References Cited

FOREIGN PATENT DOCUMENTS 2647368 5/1977 Fed. Rep. of Germany .

OTHER PUBLICATIONS

Brustier et al., *Chem. Abstracts*, vol. 77, (1972), No. 56679k.

*Primary Examiner*—Robert W. Ramsuer
*Attorney, Agent, or Firm*—Ladas & Parry

[57] ABSTRACT

The present invention relates to new derivatives of pyrrole of formula:

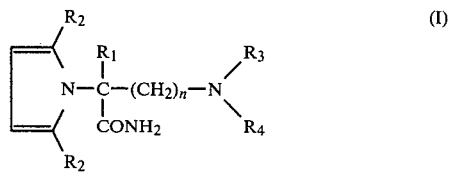

in which:
R$_1$ represents an atom of hydrogen, a lower alkyl group, a phenyl radical or a pyridyl-2 radical,
R$_2$ represents an atom of hydrogen or a lower alkyl radical
R$_3$ and R$_4$ represent a lower alkyl or cycloalkyl radical or the radical

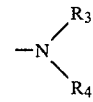

is a heterocyclic amine radical, and
n is equal to 2 or 3;

The invention concerns drugs having an antiarrhythmic activity and an activity as blood platelet anti-aggregant, containing said derivatives.

5 Claims, No Drawings

PYRROLE AMIDES AND THERAPEUTIC USE THEREOF

The present invention relates, as new industrial products, to derivatives of pyrrole, as well as to the methods for preparing them and application thereto in therapeutics.

The novel compounds according to the invention correspond to the general formula:

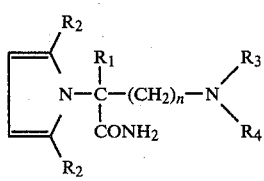

in which:

$R_1$ represents an atom of hydrogen, a lower alkyl group, a phenyl radical or a pyridyl-2 radical;

$R_2$ designates an atom of hydrogen or a lower alkyl radical;

$R_3$ and $R_4$, which are identical or different, each represent a lower alkyl or cycloalkyl radical or the group

designates a cyclic amine radical comprising 1 or 2 cycles and being able to possess a second heteroatom and comprise substituents; and n is equal to 2 or 3.

When the group

is a cyclic amine radical, the following may be mentioned among said amines: pyrrolidine, piperidine, dimethyl-2,6 piperidine, morpholine, piperazine and the radical

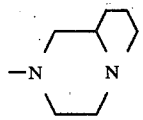

In the present invention, lower alkyl group designates straight or branched alkyl groups having from 1 to 6 atoms of carbon.

The compounds (I) yield soluble salts with the mineral or organic acids. These salts, with the pharmaceutically acceptable acids, form an integral part of the invention.

According to the nature of the substituent $R_1$, the compounds (I) may be obtained by one of the following methods:

When $R_1$ designates hydrogen, the compounds (I) may be obtained according to two processes.

Method $A_1$

The different steps of the process are indicated in the following reaction diagram:

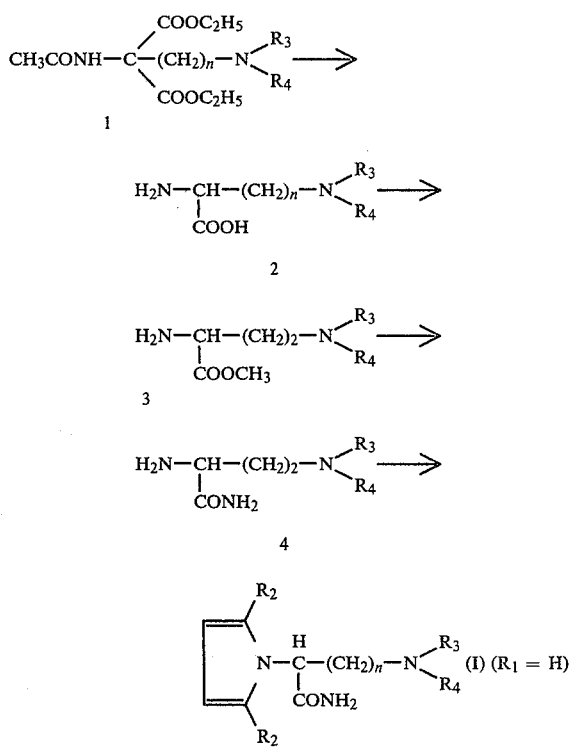

The compound 1 is prepared by alkylation according to the known processes of ethyl acetamidomalonate. By saponification of the compound 1 in an alkaline medium, the corresponding malonic acid is obtained which easily decarboxlates by heating in an acid medium to yield the substituted butyric acid 2. The latter is esterified by a known process into methyl ester 3. The ester 3 is converted into the corresponding amide 4 by action of ammonia according to a known process. Finally, the amide 4 is converted into compound (I) by heating with a γ-diketone $$R_2C-CH_2CH_2C-R_2$$
$$\parallel \qquad \qquad \parallel$$
$$O \qquad \qquad O$$

in the acetic acid.

In the particular case of $R_2=H$, compound (I) may be obtained by heating the amide 4 with dimethoxy-2,5 tetrahydrofuran in absolute alcohol in the presence of acetic acid.

Method $A_2$

The different steps of the process are indicated in the following reaction diagram:

$$Br-(CH_2)_n-CH-COOCH_3, HCl \longrightarrow$$
$$\qquad \qquad | $$
$$\qquad \qquad NH_2$$
$$5$$

-continued

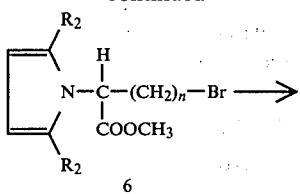
6

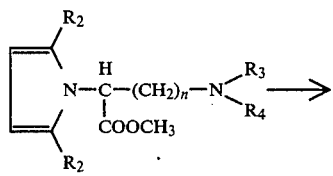
7

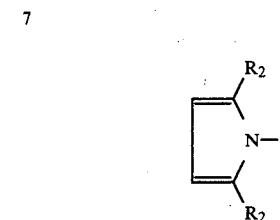
(I) (R₁ = H)

The hydrochloride of methyl amino-2 bromo-4 butyrate 5[Tetrahedron, 25, 5971–81, (1969)] is converted into corresponding pyrrolic derivative 6 either by action of a γ-diketone, or by action of the dimethoxy-2,5 furan, as indicated in method A₁.

By action of an amine

on 6 in solution in an inert solvent, such as benzene or toluene, the compound 7 is obtained which, by amidification by ammonia, leads to the products (I), (R₁=H).

Method B

When R₁ represents a phenyl group or a pyridyl-2 group, the compounds (I) are obtained according to the following reaction diagram from a product 8,

R₁CH—A,
|
NH₂ in which R₁ designates a phenyl or pyridyl-2 group and A designates a group derived from the acid function, namely a nitrile group -C≡N or an ester group -COO-Alk (Alk represents a methyl or ethyl group).

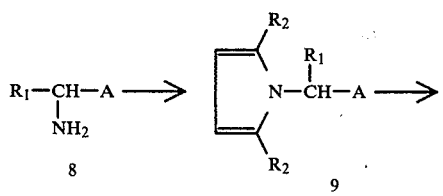
8    9

-continued

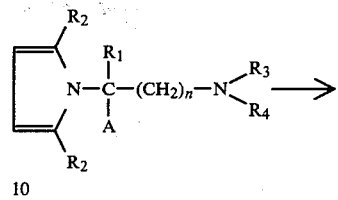
10

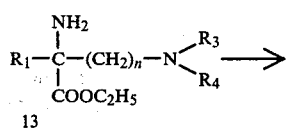
(I) (R₁ = phenyl or pyridyl-2)

As in the methods A₁ and A₂, the amino compound 8 is converted into the corresponding pyrrolic compound 9 by action of a γ-diketone or by action of the dimethoxy-2,5 tetrahydrofuran.

The compound 9 is alkylated by

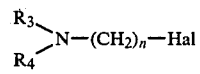

(Hal designating a halogen) in an inert solvent such as toluene and in the presence of a base such as sodium hydride and yields compound 10. In the latter, the group A is converted into an amide group. When A represents a nitrile group, the latter is hydrolysed for example by heating with sodium hydroxide in dilute alcoholic solution. When A designates an ester group, the latter is converted into amide by action of ammonia or, in the case of voluminous amines, by action of the complex salt formed by the aluminium hydride and the ammonia in the tetrahydrofuran.

Method C

When R₁ is an alkyl group, the different steps of the synthesis are shown in the following reaction diagram:

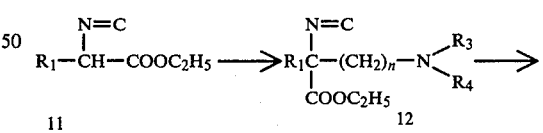
11    12

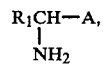
13

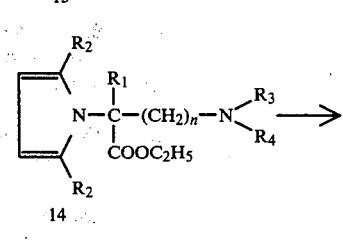
14

-continued

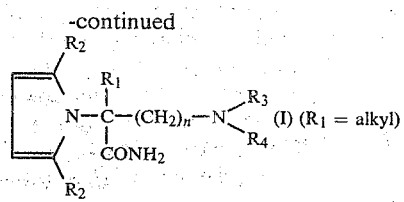

The starting product 11 is an α-isocyanoester. The products of this type are known or may be prepared according to known processes, particularly by action of the phosgene on the corresponding α-formylaminoester compounds.

Compound 11 is alkylated by

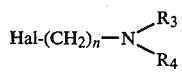

in a suitable solvent and in the presence of an alkaline agent to lead to compound 12. The latter treated by an acid in organic solution leads to the amine 13. The latter is converted into pyrrolic derivative 14, as has been indicated previously.

Finally, the ester function is converted into amide by action of ammonia or, preferably, by using the complex salt formed by the hydride of lithium-aluminium and ammonia in the tetrahydrofuran.

The following non-limiting examples are given by way of illustration for the preparation of the compounds (I).

EXAMPLE 1

Method A₁

(Dimethyl-2,5 pyrrolyl-1)-2 diisopropylamino-4 butyramide (CM 7753)

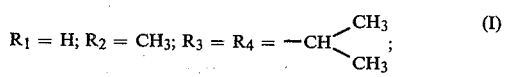

n=2

(1) Amino-2 diisopropylamino-4 burytic acid

The mixture of 17.3 g of ethyl (diisopropylamino-2 ethyl)-2 acetamidomalonate and 4.4 g of sodium hydroxide in 300 ml of water and 150 ml of ethanol at 96° is refluxed for 3 hours. The mixture is evaporated to dryness and the residue is taken up in 200 ml of 2 N hydrochloric acid; the mixture is refluxed for 5 hours.

After cooling, the mixture is neutralised to pH 7 by the addition of a solution of sodium hydroxide. The mixture is evaporated to dryness and the residue is taken up in chloroform. The insoluble sodium chloride is filtered, the solution is dried over sodium sulfate and is evaporated to dryness.

The residue constituted by a brownish solid (11.3 g) is used as such for the following operation.

(2) Methyl amino-2 diisopropylamino-4 butyrate 22 g of thionyl chloride are added to 30 ml of methanol, with cooling, so as to maintain the temperature below −5° C., then 37,7 g of the acid obtained hereinabove are added in portions, always maintaining the temperature lower than −5° C. When the addition is finished, the temperature is allowed to return to ambient temperature, then the mixture is heated for 2 hours at 40° C. The methanol is evaporated and the residue is taken up in the minimum of water; 500 ml of ether are added and, with stirring, the aqueous phase is saturated with potassium carbonate. The ethereal phase is separated and the aqueous phase is re-extracted with ether. The ethereal extracts are combined, dried over sodium sulfate and evaporated to dryness.

A yellow liquid remains (13 g) used as such for the following operation.

(3) Amino-2 diisopropylamino-4 butyramide

In an autoclave cooled by an ice bath, the solution of 3 g of the preceding ester is placed in 20 ml of absolute ethanol and a current of ammonia is bubbled therein for 1 hour. The autoclave is closed and heated at 150° C. for 36 hours.

The alcohol is evaporated and the residue is taken up in water and chloroform. The organic phase is separated and washed with water. The aqueous phases are evaporated to dryness and the residue is extracted with chloroform. The combined chloroform extracts are dried over sodium sulfate and evaporated to dryness.

A coloured liquid remains (1.54 g) used without purification for the following operation.

(4) CM 7753

The previously obtained oil (1.54 g) and 0.98 g of hexanedione-2,5 is dissolved in 40 ml of acetic acid and the mixture is heated at 100° C. for 3 hours. The solvent is evaporated then alkalinized with diluted sodium hydroxide. It is extracted with ether, the ethereal phase is dried over sodium sulfate and evaporated to dryness. A blackish, viscous liquid is obtained which is chromatographed over an alumina column, eluting by the 70:30 (vol/vol) mixture of hexane-ethyl acetate.

A yellowish solid (1 g) is obtained which is recrystallised in isopropylic ether. Finally, colourless crystals are obtained; m.p. 71°–72° C.

EXAMPLE 2

Method A₂

(Dimethyl-2,5 pyrrolyl)-1 (diaza-1,4 bicyclo[4.3.0]nonyl-4)-4 butyramide (CM 40018)

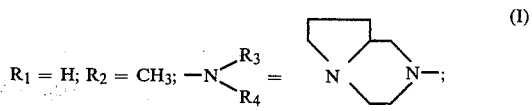

n=2

(1) methyl (dimethyl-2,5 pyrrolyl-1)-2 bromo-4 butyrate

The mixture of 30 g of hydrochloride of methyl amino-2 bromo-4 butyrate, 17.7 g of hexanedione-2,5 and 10.6 g of anhydrous sodium acetate in 500 ml of acetic acid is heated at 100° C. for 3 hours. The acetic acid is evaporated in vacuo, then the residue is taken up with water and ether. The ethereal layer is separated and washed successively with water, with a solution of sodium bicarbonate and again with water. The solution is dried over sodium sulfate, then the solvent is evaporated to dryness.

The residue is chromatographed over a silica column eluting with the 9:1 (vol/vol) pentane-ethyl acetate mixture. By evaporation, a crystallised solid is obtained which is washed with petroleum ether. Weight: 15.1 g; m.p. 79° C.

(2) Methyl (dimethyl-2,5 pyrrolyl-1)-2 (diaza-1,4 bicyclo[4.3.0]-nonyl-4)-4 butyrate The mixture of 11 g of the ester obtained hereinabove and 10.1 g of diaza-1,4 bicyclo-[4.3.0]-nonane in 150 ml of toluene is refluxed for 48 hours. After cooling, the organic solution is washed with water, dried over sodium sulfate and the solvent is evaporated to dryness in vacuo.

The residue is chromatographed over an alumina column, eluting with the 95:5 (vol/vol) pentane-ethyl acetate mixture.

An oil (9 g) is obtained, used as such for the following operation.

(3) CM 40018

In the suspension of 1.71 g of lithium-aluminium hydride in 100 ml of anhydrous tetrahydrofuran, a current of dry ammonia gas is bubbled until the end of precipitation. The solution of 3.19 g of the ester obtained in the preceding paragraph in 40 ml of tetrahydrofuran is then added with stirring, then the mixture is heated at 55°–60° C. for 3 hours 30 minutes. The mixture is cooled by an ice bath and hydrolysed by a 40% sodium hydroxide solution. It is filtered and the solvent is evaporated to dryness. The residue is taken up in chloroform and water. The organic phase is separated and the aqueous phase is again extracted with chloroform. The organic extracts are combined and dried over sodium sulfate. The solvent is evaporated to dryness.

The solid residue is recrystallised in ethyl acetate (1.7 g); m.p. 166°–167° C.

EXAMPLE 3

Method B

Phenyl-2 (pyrrolyl-1)-2 diisopropylamino-4 butyramide (CM 7611)

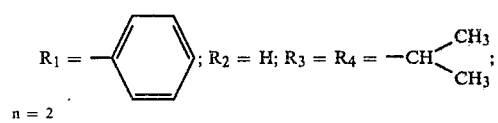

n = 2

(1) Phenyl-2 (pyrrolyl-1)-2 acetonitrile

The mixture of 16.85 g of hydrochloride of amino-2 phenyl-2 acetonitrile, 8.2 g of molten sodium acetate and 26.4 g of dimethoxy-2,5 tetrahydrofuran in 200 ml of acetic acid is heated at 100° C. for 2 hours. The acetic acid is then evaporated in vacuo to dryness and the residue is taken up in ether. The precipitated solid is dried without heat, then the ethereal solution is washed with water. The ethereal solution is dried over sodium sulfate and the ether is evaporated to dryness.

The residue is distilled under a high vacuum, b.p./0.03 mm of mercury; 108°–112° C. The distillate crystallises; it is recrystallised in hexane; weight: 8 g; m.p. 51° C.

(2) Phenyl-2 (pyrrolyl-1)-2 diisopropylamino-4 butyronitrile

The mixture of 5.16 g of the nitrile obtained previously, 1.3 g of sodium amide and 5.1 g of chloro-1 diisopropylamino-2 ethane in 150 ml of toluene is heated to reflux for 2 hours. After cooling, the organic solution is extracted with a dilute solution of hydrochloric acid. The acid aqueous phase is separated, is alkalinised with sodium hydroxide and extracted with ether. The ethereal solution is dried and the solvent is evaporated to dryness. The residue is chromatographed over a silica column, eluting by the 8:2 (vol/vol) hexane-ethyl acetate mixture.

6.35 g of the expected product is obtained, used as such for the following operation.

(3) CM 7611

The solution of 6.07 g of the nitrile obtained previously and 22.5 g of potash in 180 ml of 96° ethanol and 45 ml of water is heated to reflux for 5 hours.

After evaporation of the alcohol, the residue is taken up in water and chloroform. The organic phase is separated, is dried over sodium sulfate and the solvent is evaporated to dryness. The residue is chromatographed over an alumina column. By eluting with the 8-2 (vol/vol) hexane-ethyl acetate mixture, an impurity is eliminated then, with the 1:1 (vol/vol) mixture of hexane-ethyl acetate, the expected product is eluted.

By recrystallisation in isopropyl ether, colourless crystals are obtained (4.5 g); m.p. 103°–104° C.

EXAMPLE 4

Method B (Pyridyl-2)-2(pyrrolyl-1)-2 diisopropylamino-4 butyramide (CM 7954)

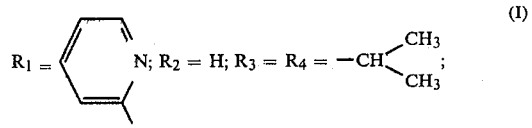

n = 2

(1) Ethyl (pyridyl-2)-2 (pyrrolyl-1)-2 acetate

The mixture of 22 g of amino-2 (pyridyl-2)-2 acetate of ethyl and 32.3 g of dimethoxy-2,5 tetrahydrofuran in 300 ml of absolute ethanol and 150 ml of acetic acid, is heated to reflux for 3 hours.

The solvents are evaporated to dryness in vacuo and the residue is taken up in an aqueous solution of sodium bicarbonate. The solution is extracted with ether and is dried over sodium sulfate. The solvent is evaporated to dryness and the residue is distilled under reduced pressure; b.p./0.01 mmHg: 115°–122° C.

The distillate crystallises; m.p. 75°–76° C.; weight: 11.3 g.

(2) Ethyl (pyridyl-2)-2 (pyrrolyl-1)-2 diisopropylamino-4 butyrate

The mixture of 15.65 g of the preceding ester, 3.57 g of sodium hydride and 12.4 g of chloro-1 diisopropylamino-2 ethane in 500 ml of anhydrous toluene is heated at 100° C. in an atmosphere of nitrogen, for 1 hour 30 minutes.

After cooling, the solution is washed with water, dried over sodium sulfate and the solvent is evaporated to dryness. Chromatography is carried out over an alumina column. By eluting with the 95:5 (vol/vol) pentane-ethyl acetate mixture, 17.8 g of the expected product is obtained; m.p. 45°–47° C.

(3) CM 7954

In the suspension of 1.14 g of double hydride of lithium-aluminium in 60 ml of anhydrous tetrahydrofuran, a stream of dry ammonia is bubbled until the complex has finished precipitating. The solution of 7.14 g of the ester obtained hereinabove is added in 40 ml of tetrahydrofuran and the mixture is left, with stirring, at ambient temperature for 24 hours.

Hydrolysis is carried out by addition of 40% solution of sodium hydroxide, the insoluble matter is filtered and the tetrahydrofuran is evaporated to dryness. The residue is taken up in ether, the organic solution is washed with water, dried over sodium sulfate and evaporated to dryness. The residue is recrystallised in isopropylic ether.

Colourless crystals are obtained (3.35 g); m.p. 128°–129° C.

EXAMPLE 5

Method C

Methyl-2 (pyrrolyl-1)-2 diisopropylamino-4 butyramide (CM 40019)

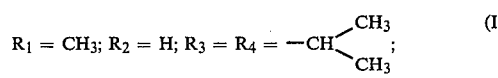

n=2

(1) ethyl isocyano-2 methyl-2 diisopropylamino-4 butyrate 14.54 g of ethyl isocyano-2 propionate and 19.75 g of chloro-1 diisopropylamino-2 ethane are dissolved in 300 ml of anhydrous ether and 120 ml of dimethylsulfoxide. Cooling is effected with an ice bath and a suspension of 5.73 g of 55–60% sodium hydride in 90 ml of anhydrous ether is added by fractions. The addition terminated, the mixture is refluxed for 2 hours. After cooling, the reaction mixture is poured in 300 ml of glacial water. The organic phase is decanted and the aqueous phase is extracted three times with ether. The organic extracts are combined and washed with water. Drying is effected over sodium sulfate and the solvent is evaporated to dryness.

The residue is distilled under reduced pressure; B.p./0.7 mmHg: 102°–106° C.; weight: 16 g.

(2) Ethyl amino-2 methyl-2 diisopropylamino-4 butyrate

In 60 ml of absolute ethanol to which 1.57 g of water is added, hydrogen chloride is bubbled up to saturation.

The solution is cooled below $-10°$ C. and 16 g of the isocyanate obtained previously dissolved in 18 ml of absolute ethanol are added, then the temperature is allowed to rise progressively up to ambient temperature and the mixture is left to stand for 20 hours at this temperature. The solvent is evaporated to dryness in vacuo and the residue is taken up in ether. The ethereal solution is washed with a saturated solution of potassium bicarbonate in water. The aqueous phase is separated and extracted with ether. The ethereal extracts are combined, dried over potassium carbonate and the solvent is evaporated to dryness.

An oil remains (14.75 g) used as such for the following operation.

(3) Ethyl methyl-2 (pyrrolyl-1)-2 diisopropylamino-4 butyrate

The mixture of 2 g of the aminoester obtained hereinabove and 2.17 g of dimethoxy-2,5 tetrahydrofuran in 30 ml of absolute ethanol and 15 ml of acetic acid is heated to reflux for 18 hours. The solvents are evaporated to dryness in vacuo and the residue is taken up in ether. The ethereal solution is washed with water, then with an aqueous solution of sodium bicarbonate and again with water. The substance is dried over sodium sulfate and the solvent is evaporated to dryness. Chromatography is carried out on an alumina column. By eluting with the 98:2 (vol/vol) pentane-ethyl acetate mixture, 1.1 g of the expected product is obtained.

(4) CM 40019

The modus operandi is as indicated in Example 4, paragraph 3, using the ester prepared previously and reducing the duration of reaction to 1 hour instead of 24 hours.

By the same treatment, the expected amide is obtained with a yield of 60%; m.p. 79°–80° C. [petroleum ether (b.p. 40°–65° C.)].

EXAMPLES 6 to 11

By operating according to Examples 1 to 5, but by varying the reagents, the products shown in Table I hereinbelow are obtained.

For each of the products (I), the code number, the nature of the substituents, the method of preparation used and finally the melting point and crystallisation solvent, are indicated.

TABLE I

| Code No. | $R_1$ | $R_2$ | n | $R_3$ | $R_4$ | Method | m.p. °C. (crystallisation solvent) |
|---|---|---|---|---|---|---|---|
| 7640 | phenyl | —CH$_3$ | 2 | —CH(CH$_3$)$_2$ | —CH(CH$_3$)$_2$ | B | 106–107 (petroleum ether) |
| 40017 | H | —CH$_3$ | 2 | morpholino (N, O ring) | | A$_2$ | 124–125 (ethyl acetate) |
| 40002 | H | —CH$_3$ | 2 | —C$_2$H$_5$ | —C$_2$H$_5$ | A$_1$ | 88–89 (isopropyl ether) |

TABLE I-continued

| Code No. | R₁ | R₂ | n | R₃ | R₄ | Method | m.p. °C. (crystallisation solvent) |
|---|---|---|---|---|---|---|---|
| 7921 | H | H | 2 | —CH(CH₃)₂ | —CH(CH₃)₂ | A₁ | 68–69 (hexane) |
| 40020 | H | —C₂H₅ | 2 | " | " | A₁ | isolated in the form of hydrochloride 122–124 (methylethylketone) |
| 40021 | —CH₂—CH(CH₃)₂ | H | 2 | —CH(CH₃)₂ | —CH(CH₃)₂ | C | isolated in the form of hydrochloride 184–186 (isopropanol) |
| 40105 | H | —CH₃ | 2 | \[piperidine ring with 2,6-dimethyl, as N$_n$\] | | A₁ | isolated in the form of tosylate, 110–112 (isopropanol) |
| 40169 | H | —CH₃ | 2 | cyclohexyl | —CH(CH₃)₂ | A₁ | isolated in the form of fumarate 165–166 (ethanol) |
| 40176 | H | —CH₃ | 2 | —CH₂CH₂CH₃ | —CH₂CH₂CH₃ | A₁ | isolated in the form of hydrochloride 198–199 (isopropanol) |
| 40178 | H | —CH₃ | 2 | —CH(CH₃)—CH₂CH₃ | —CH(CH₃)—CH₂CH₃ | A₁ | isolated in the form of fumarate, 147–148 (acetone) |
| 40201 | H | —CH₃ | 3 | —CH(CH₃)₂ | —CH(CH₃)₂ | A₁ | 80–81 (isopropylic ether) |
| 40261 | H | —CH₃ | 2 | cyclohexyl | cyclohexyl | A₁ | 95–97 (pentane) |

The products of the invention have been studied in animal pharmacology and in particular with a view to demonstrating their properties.

Arrhythmic properties

Protocol

The anti-arrythmic power of these molecules was assessed on an animal model of ventricular arrythmia.

Mongrel dogs are anaesthesized then subjected to the positioning, by retrograde catheterism, of a metal spiro in the coronary bed. At the same time, a micro-emitter frequency modulator is fixed to the animal's back and connected to two precordial electrodes.

The animal returned to its box then shows a progressive thrombosis of the anterior interventricular artery. Thus a localised, transmural myocardial infarction is constituted, generating an abnormal, but repetitive electrical activity: ventricular tachycardia.

In this state, the drugs are administered per os (P.O.) and the telemetered system enables the development of the arrythmia to be followed in real time.

The sinusal systolic complexes and pathologies are permanently counted by electronic processes.

Thus, the quality and duration of action of the product may be quantified.

Results

The results concerning various products are shown in Table II hereinbelow.

The activity of the tested products on the ventricular tachycardia is expressed either by the re-establishment of the sinusal rhythm, or by a considerable improvement in the ratio:

$$\frac{\text{number of abnormal complexes}}{\text{number of sinusal complexes}}$$

TABLE II

| Products CM No. | Dose, mg/kg P.O. | Number of animals | Effect on the ventricular tachycardia |
|---|---|---|---|
| CM 7611 | 50 | 3 | Sinusal rhythm or improvement between 70–90% from 3 or 4 hours. |

TABLE II-continued

| Products CM No. | Dose, mg/kg P.O. | Number of animals | Effect on the ventricular tachycardia |
|---|---|---|---|
| CM 7753 | 50 | 4 | Sinusal rhythm or 90% improvement from 1½ hrs to 5 hours |
| CM 7640 | 50 | 1 | Sinusal rhythm or 90% improvement for 90 minutes |

Activity as blood platelet anti-aggregant

Experimental protocol

In vitro and ex vivo studies of the anti-aggregant activity were made according to Born's turbidiuretic technique.

The in vitro studies were made on platelet-rich plasma (PRP) prepared from human venous blood.

The various solutions of the products to be tested were prepared extemporaneously. The CM 7753, 7611, 7640, 7921, 7954, 40018, 40020 were dissolved at a concentration of $2 \times 10^{-2}$ M in acetone.

$2 \times 10^{-3}$ M aqueous solutions were prepared for the CM 40169, 40178, 2 μl of the acetone solutions of the products or 40 μl of the aqueous solutions are incubated for 10 minutes at 37° C. with, respectively, 388 and 350 μl of PRP. After this period of incubation, 10 μl of the solution of collagen at 40 μg/ml are added. For controls, 2 μl of acetone or 40 μl of distilled water are used.

The ex vivo studies in the baboon were made solely on the anti-aggregant activity of the CM 7753. In this case, the CM 7753 is administered orally at a rate of 50 mg/kg/day for a period of 5 days.

Blood samples for analysing the platelet aggregation were made before the product was administered, 2 hours after administration of 50 mg/kg on day 1 and 2 hours after the last administration of day 5.

Platelet aggregation was quantified by the graphic determination of the maximum amplitude of aggregation (MA).

The results are expressed in % of inhibition of this parameter calculated with respect to the control (100% aggregation).

Results

In vitro study

From the products studied, two proved particularly active with respect to the platelet aggregation induced by the collagen. These are CM 7640 and CM 7611 (IC50 approximately situated at 30 μM).

The products CM 7753 and 7954 inhibit at 50% the platelet aggregation at a concentration close to 100 μM. Other products, CM 40018, 40020, 40169, 40178 and 7921 inhibit the phenomenon of aggregation less strongly (20 to 30% inhibition at a concentration of 100 μM).

Ex vivo study

Studied under ex vivo conditions, the CM 7753 particularly inhibits the platelet aggregation induced by the collagen.

In four baboons used in the study, 100% of inhibition was obtained after 5 days of treatment at the dose of 50 mg/kg/day. An anti-aggregant activity of lesser importance is also observed with respect to ADP.

These results show that the products according to the invention are endowed with a strong activity on experimental arrhythmia and present a considerable blood platelet anti-aggregant activity. Consequently, the products (I) may be used in human therapeutics as protectors of the myocardium for correcting disorders in the ventricular rhythm of ischaemic origin as well as disorders in platelet aggregation.

The products may be presented in galenic forms of administration to be taken orally (tablets, capsules, etc.) and parenterally (injectable ampoules).

The dose necessary for a platelet anti-aggregant activity or for restoring the sinusal rhythm in human beings is between about 50 and 150 mg of the I.V. route and about 400 and 800 mg by the oral route, per day.

By way of example, the following gelenic preparation is indicated:

| Tablets | |
|---|---|
| CM 7753 | 0.200 g |
| Microcrystalline cellulose | 0.140 g |
| Lactose | 0.140 g |
| Magnesium stearate | 0.020 g |

What is claimed is:

1. Derivatives of pyrrole of formula

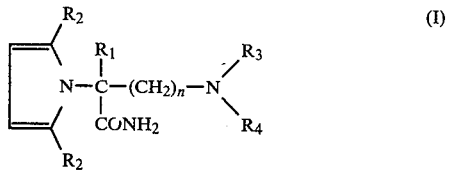

in which:

R₁ represents an atom of hydrogen, a lower alkyl group, a phenyl radical or a pyridyl-2 radical, R₂ represents an atom of hydrogen or a lower alkyl radical, R₃ and R₄, which are identical or different, each represent a lower alkyl or cycloalkyl radical, or the group

designates a cyclic amine radical comprising one or 2 cycles and being able to possess a second heteroatom on dimethyl-2,6-piperidine and n is equal to 2 or 3, as well as the salts of these derivatives with a pharmaceutically acceptable acid, 2. The derivatives of claim 1, wherein the group

is chosen from pyrrolidine, piperidine, dimethyl-2,6 piperidine, morpholine, piperazine and the amine of formula:

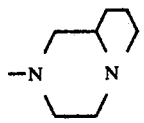

3. A process for treating arrhythmia and blood platelet aggregation in a mammal comprising administering an effective amount of a compound as defined in claim 1.

4. A process according to claim 3, wherein said compound is administered by oral administration at a dose of 400 to 800 mg. per day.

5. A process according to claim 3, wherein the compound is administered by parenteral administration at a dose of 50 to 150 mg. per day.

* * * * *